July 14, 1953 H. M. TIRET Plant Pat. 1,201
FUCHSIA PLANT
Filed Feb. 27, 1952
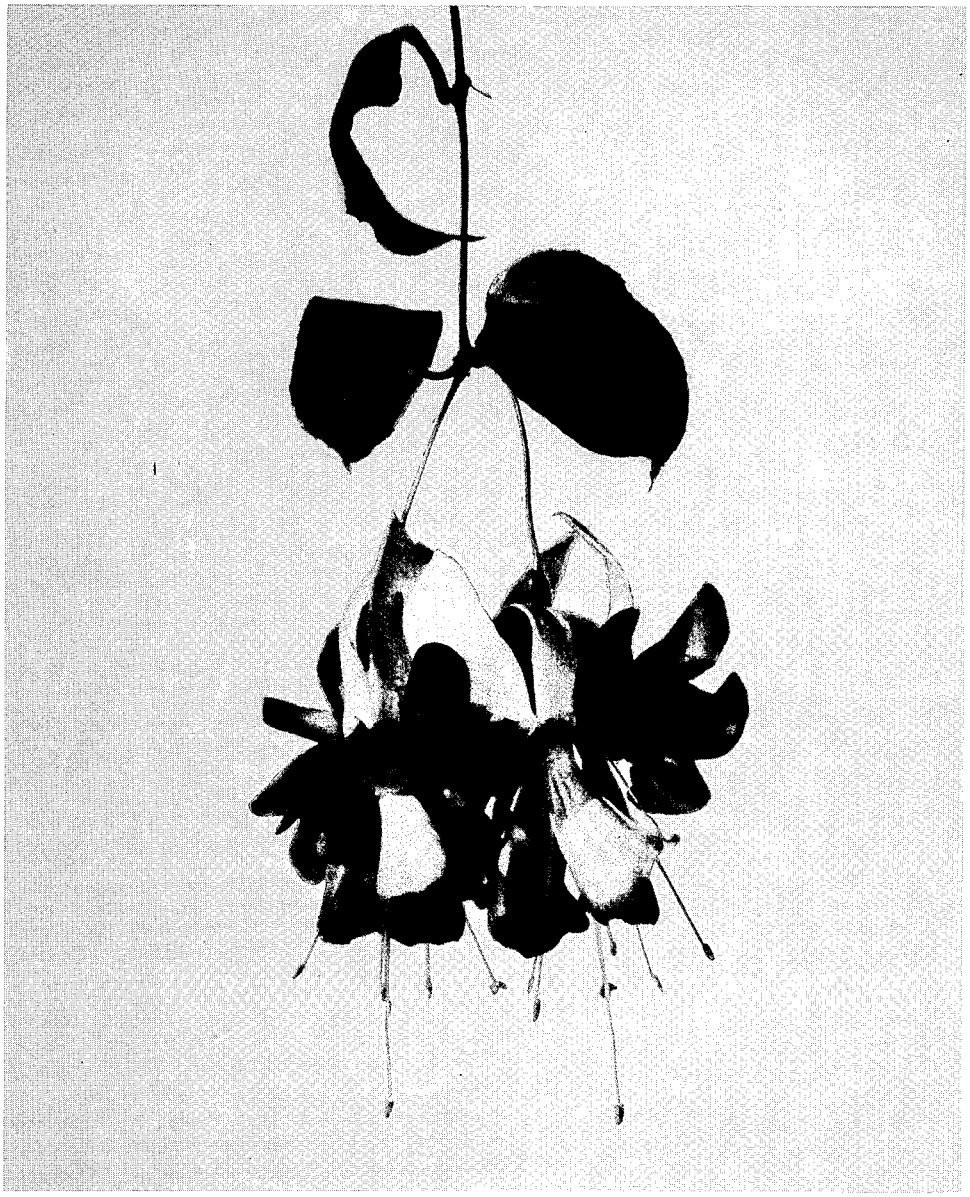
Inventor
Horace M. Tiret Patented July 14, 1953

Plant Pat. 1,201

UNITED STATES PATENT OFFICE 1,201

FUCHSIA PLANT

Horace M. Tiret, San Francisco, Calif.

Application February 27, 1952, Serial No. 273,704

1 Claim. (Cl. 47—60)

This invention relates to a new and improved fuchsia plant, the principal new and different characteristics of which are the exceptionally long slender tube, and the long, recurved sepals which tend to spread in all directions, creating a grotesque appearance. The long, loosely formed petals add to that effect.

The plant was derived as a hybrid from Uncle Jules (unpatented), a fuchsia introduced by Victor Reiter, Jr., and San Francisco (unpatented), introduced by the late Victor Reiter, Sr. The fuchsia plant is distinguished principally by its green, deeply veined foliage, vigorous habit of growth, and distinctive deep crimson coloring, which has not previously been found in this combination and form in any fuchsia plant, and has been asexually reproduced at Palo Alto, Santa Clara County, California, by cuttings which retained the characteristics of the parent fuchsia.

The plant is a trailing variety and grows vigorously, throwing numerous branches in the process of growth. When the plant blooms, the exceptionally long, crimson buds open into large, semi-double flowers. The bud is deep crimson (Horticultural Color Chart 22). The petals are deep crimson from the base to about the center, with the lower portion deep rhodamine purple (Horticultural Color Chart 29). The flower has no fragrance.

In the accompanying drawing, the figure shows a typical branch tip including both a bud and fully opened blossom, the drawing representing approximately actual size.

A detailed description of this new variety of fuchsia plant follows:

*Habit of growth.*—Strong trailing variety which throws out branches from the roots and whose branches in turn are self-branching to form a full basket. Flowers occur both along the stem and at the tips of the branches.

*Foliage.*—Medium large green leaves deeply veined, having a smooth surface and evenly spaced along the branch. The leaves are oval shaped with pointed tips. The buds are exceptionally long and slender in shape, being well pointed, and are colored crimson.

*Flower.*—The flower is semi-double of exceptionally large size for the genus. The corolla is loosely formed. The flower is strongly resistant to wilting at high atmospheric temperature, but grows equally well in the cooler coastal climate of the west. The color is deep crimson (Horticultural Color Chart 22) shading to rhodamine purple (Horticultural Color Chart 29) at the base of the petals.

*Ovary.*—Long, slender, and green in color.

*Tube.*—Slender and exceptionally long. Deep crimson in color. (Horticultural Color Chart 22.)

*Petals.*—From four to nine petals occur to each flower. As the flower matures, the petals retain their loosely formed appearance. The petals are deep crimson, shading to rhodamine purple, all as above described.

*Stamens.*—The stamens are exceptionally long, approximately 2⅝ inches in length measured from the seed pod, and of a dark maroon color, and terminate short of the long pistil, which is approximately 4⅝ inches in length, measured from the seed pod, having a maroon tip which hangs below the cluster of stamens.

*Sepals.*—The sepals are exceptionally long and slender, and recurved with a tendency to spread indiscriminately, and without pattern, in all directions. Coloring on both sides is deep crimson. The texture on the upper surface is smooth, on the under surface crepe-like.

*Parentage.*—Uncle Jules (unpatented) by Victor Reiter, Jr., and San Francisco (unpatented) by the late Victor Reiter, Sr.

It is noted that the foliage and flowers will vary somewhat with the seasons and growing conditions; however, the fuchsia plant is clearly differentiated from others by its form resulting from the combination of the exceptionally long slender tube, the long, recurved sepals with their tendency to spread in all directions, and the long loosely formed petals.

Having thus disclosed my discovery I claim:

The new and distinct variety of fuchsia plant herein described and illustrated, characterized by a distinctive form resulting from the combination of the exceptionally long, slender tube, the long, recurved sepals tending to spread in all directions without pattern, and which lend a grotesque appearance to the plant, and the loosely formed petals.

HORACE M. TIRET.

References Cited in the file of this patent

UNITED STATES PATENTS

| Number | Name | Date |
|---|---|---|
| Pl.P. 1,110 | Waltz | July 1, 1952 |